(12) United States Patent
Stroefer et al.

(10) Patent No.: US 7,671,240 B2
(45) Date of Patent: Mar. 2, 2010

(54) METHOD FOR PRODUCING POLYOXYMETHYLENE DIMETHYL ETHERS FROM METHANOL AND FORMALDEHYDE

(75) Inventors: Eckhard Stroefer, Mannheim (DE); Hans Hasse, Kaiserslautern (DE); Sergej Blagov, Stuttgart (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 247 days.

(21) Appl. No.: 11/917,528

(22) PCT Filed: Jun. 12, 2006

(86) PCT No.: PCT/EP2006/063095

§ 371 (c)(1),
(2), (4) Date: Dec. 14, 2007

(87) PCT Pub. No.: WO2006/134088

PCT Pub. Date: Dec. 21, 2006

(65) Prior Publication Data

US 2008/0207954 A1      Aug. 28, 2008

(30) Foreign Application Priority Data

Jun. 15, 2005   (DE) ...................... 10 2005 027 701

(51) Int. Cl.
*C07C 41/56*   (2006.01)
*C08G 2/08*    (2006.01)
(52) U.S. Cl. .................................. 568/618
(58) Field of Classification Search ........................ None
See application file for complete search history.

(56) References Cited

U.S. PATENT DOCUMENTS

| | | | |
|---|---|---|---|
| 2,449,469 A | 9/1948 | Gresham et al. | |
| 5,746,785 A | 5/1998 | Moulton et al. | |
| 6,392,102 B1 | 5/2002 | Hagen et al. | |
| 6,534,685 B1 | 3/2003 | Patrini et al. | |

FOREIGN PATENT DOCUMENTS

EP        1070755        1/2001

OTHER PUBLICATIONS

U.S. Appl. No. 12/446,460, filed Apr. 21, 2009, Boehling et al.

*Primary Examiner*—Rosalynd Keys
(74) *Attorney, Agent, or Firm*—Oblon, Spivak, McClelland, Maier & Neustadt, L.L.P.

(57) ABSTRACT

Processes for preparing tri- and tetraoxymethylene glycol dimethyl ether ($POMDME_{n=3,4}$) include feeding a reaction mixture of an aqueous formaldehyde solution and methanol into a reactive evaporator and separating into a first low boiler fraction and a first high boiler fraction, recycling the first high boiler fraction into the reactor, feeding the first low boiler fraction into a first distillation column and separating into a second low boiler fraction and a second high boiler fraction, recycling the second high boiler fraction into the reactive evaporator, feeding the second low boiler fraction into a second distillation column and separating into a third low boiler fraction and a third high boiler fraction, feeding the third high boiler fraction into a phase separation apparatus and separating into an aqueous phase and an organic phase, and feeding the organic phase into a third distillation column and separating into a low and high boiler fractions.

Figure 1:
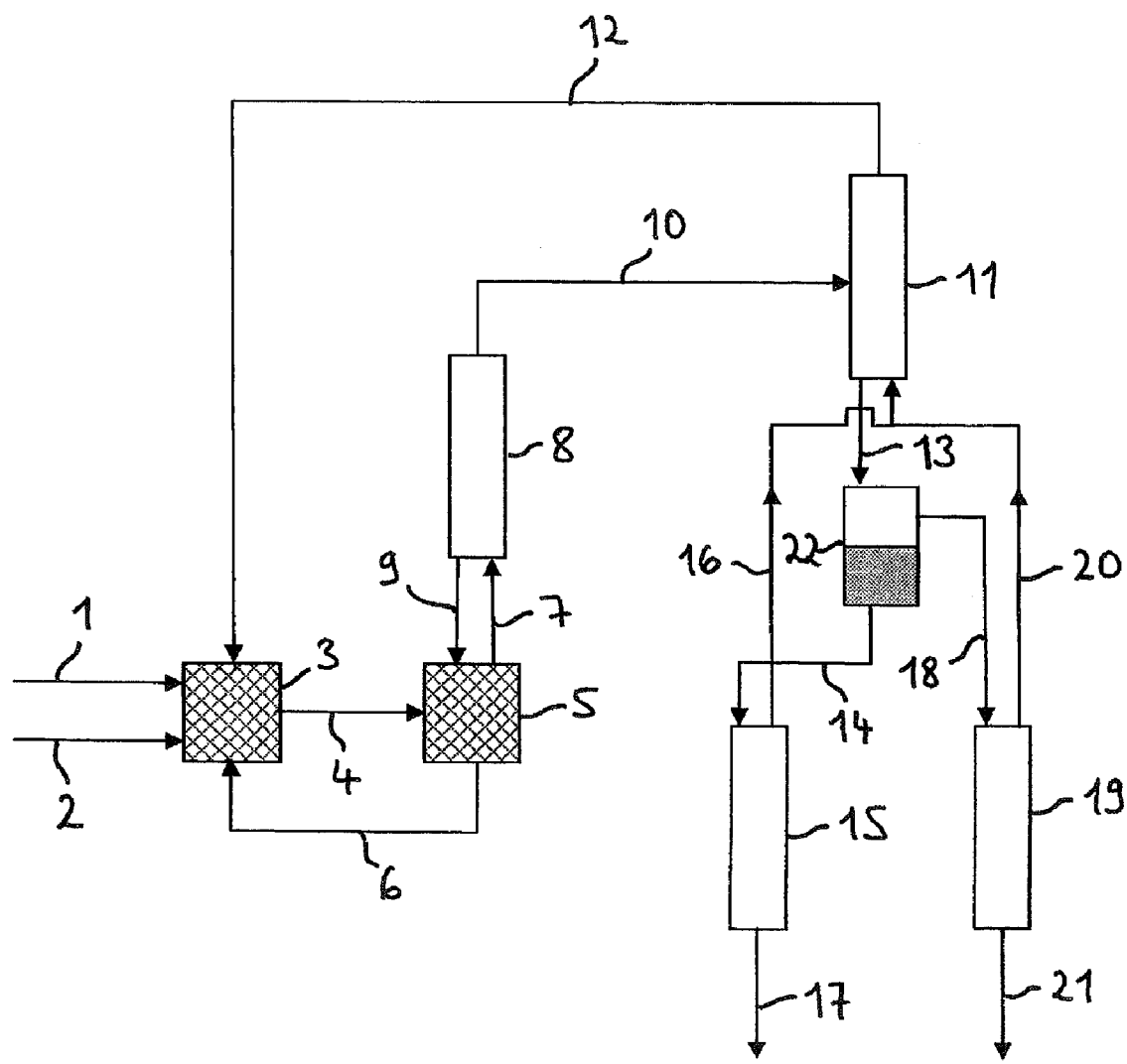

4 Claims, 1 Drawing Sheet

METHOD FOR PRODUCING POLYOXYMETHYLENE DIMETHYL ETHERS FROM METHANOL AND FORMALDEHYDE

The invention relates to a process for preparing polyoxymethylene dimethyl ethers.

Polyoxymethylene dimethyl ethers constitute a homologous series of the general formula $$CH_3O(CH_2O)_nCH_3$$

in which n is an integer $\geq 1$. Like the parent molecule of the homologous series, methylal $CH_3O(CH_2O)CH_3$ (n=1), the polyoxymethylene dimethyl ethers are acetals. They are prepared by reaction of methanol with aqueous formaldehyde in the presence of an acidic catalyst. Like other acetals, they are stable under neutral or alkaline conditions, but are attacked even by dilute acids. This converts them in a first step by hydrolysis to hemiacetals and methanol. In a second step, the hemiacetals are hydrolyzed to formaldehyde and methanol.

On the laboratory scale, polyoxymethylene dimethyl ethers are prepared by heating polyoxymethylene glycol or paraformaldehyde with methanol in the presence of traces of sulfuric acid or hydrochloric acid at temperatures of from 150 to 180° C. and reaction times of from 12 to 15 hours. This results in decomposition reactions with formation of carbon dioxide to form dimethyl ether. At a paraformaldehyde or polyoxymethylene glycol:methanol ratio of 6:1, polymers where n>100, generally n=300-500, are obtained. The products are washed with sodium sulfite solution and subsequently fractionated by fractional crystallization.

U.S. Pat. No. 2,449,469 describes a process in which methylal is heated with paraformaldehyde or a concentrated formaldehyde solution in the presence of sulfuric acid. This affords polyoxymethylene dimethyl ethers having from 2 to 4 formaldehyde units per molecule.

In recent times, polyoxymethylene dimethyl ethers have gained significance as diesel fuel additives. To reduce smoke and soot formation in the combustion of conventional diesel fuel, oxygen compounds which have only few, if any, C—C bonds, for example methanol, are added to it. However, such compounds are frequently insoluble in diesel fuel and lower the cetane number and/or the flashpoint of the diesel fuel mixture.

U.S. Pat. No. 5,746,785 describes the preparation of polyoxymethylene dimethyl ethers having a molar mass of from 80 to 350, corresponding to n=1-10, by reaction of 1 part of methylal with 5 parts of paraformaldehyde in the presence of 0.1% by weight of formic acid at a temperature of from 150 to 240° C., or by reaction of 1 part of methanol with 3 parts of paraformaldehyde at a temperature of from 150 to 240° C. The resulting polyoxymethylene dimethyl ethers are added to a diesel fuel in amounts of from 5 to 30% by weight.

EP-A 1 070 755 discloses the preparation of polyoxymethylene dimethyl ethers having from 2 to 6 formaldehyde units in the molecule by reacting methylal with paraformaldehyde in the presence of trifluorosulfonic acid. This forms polyoxymethylene dimethyl ethers where n=2-5 with a selectivity of 94.8%, the dimer (n=2) being obtained to an extent of 49.6%. The resulting polyoxymethylene dimethyl ethers are added to a diesel fuel in amounts of from 4 to 11% by weight.

U.S. Pat. No. 6,392,102 describes the preparation of polyoxymethylene dimethyl ethers by reacting a use stream comprising methanol and formaldehyde, which has been obtained by oxidation of dimethyl ether, in the presence of an acidic catalyst and simultaneous removal of the reaction products in a catalytic distillation column. This affords methylal, methanol, water and polyoxymethylene dimethyl ethers.

A disadvantage of the known processes for preparing the lower polyoxymethylene glycol dimethyl ethers (where n=1-10) is that the dimer is obtained to a quite predominant extent. The dimer formed as the main product has a low boiling point and thus lowers the flashpoint, as a result of which it is less suitable as a diesel fuel additive. Oligomers where n>8 tend to crystallize at low temperatures and are unsuitable as diesel fuel additives. In contrast, good suitability is possessed by the lower polyoxymethylene dimethyl ethers where n=3 and 4 (trioxymethylene glycol dimethyl ether and tetraoxymethylene glycol dimethyl ether). These have boiling points and flashpoints comparable to a typical diesel fuel mixture. The cold filter plugging point is also not increased.

A disadvantage of the processes which start from formaldehyde and methanol is that water is formed as a reaction product and hydrolyzes already formed polyoxymethylene dimethyl ethers in the presence of the acidic catalysts present. This forms unstable hemiacetals. The unstable hemiacetals lower the flashpoint of the diesel fuel mixture and thus impair its quality. Too low a flashpoint of the diesel fuel mixture leads to the specifications laid down by the relevant DIN standards no longer being fulfilled. Hemiacetals are, though, difficult to remove from polyoxymethylene glycol dimethyl ethers owing to comparable boiling points.

The above-described problems can be circumvented by working substantially anhydrously. This is achieved by the use of trioxane as the formaldehydic component which is reacted with methylal or dimethyl ether. However, the trioxane feedstock is more expensive than formaldehyde since the trioxane preparation in turn starts from formaldehyde as the feedstock. An additional process step is thus required.

In the process described in U.S. Pat. No. 6,392,102, the formaldehyde preparation is integrated into the polyoxymethylene dimethyl ether synthesis. In this process, formaldehyde is not prepared by oxidative dehydrogenation of methanol, in which case aqueous formaldehyde solutions with a formaldehyde content of from 20 to 60% by weight are generally obtained, but rather by oxidative dehydrogenation of dimethyl ether. This achieves formaldehyde concentrations of >60% by weight. A disadvantage is the complexity of the overall process. This comprises reactive distillations, a plurality of heterogeneously catalyzed reactors, distillation columns, absorption columns and a spray tower. This entails high development and capital costs, and also maintenance costs in the course of operation.

There is thus still a need for a process for preparing polyoxymethylene glycol dimethyl ethers which starts from commercial aqueous formaldehyde solution readily available in large amounts. Against the background of their significance as diesel fuel additives, there is in particular a need for the selective and economically viable preparation of tri- and tetraoxymethylene glycol dimethyl ether.

It is an object of the invention to provide an improved process for selectively preparing tri- and tetraoxymethylene glycol dimethyl ether which starts from aqueous formaldehyde solution.

The object is achieved by a process for preparing tri- and tetraoxymethylene glycol dimethyl ether ($POMDME_{n=3,4}$) by reacting formaldehyde with methanol and subsequently working up the reaction mixture by distillation, comprising the steps of:

a) feeding aqueous formaldehyde solution and methanol into a reactor and reacting to give a mixture a comprising formaldehyde, water, methylene glycol (MG), polyoxymethylene glycols ($MG_{n>1}$), methanol, hemiformals (HF), methylal (POMDME$_{n=1}$) and polyoxymethylene glycol dimethyl ethers (POMDME$_{n>1}$);

b) feeding the reaction mixture a into a reactive evaporator and separating into a low boiler fraction b1 comprising formaldehyde, water, methanol, methylene glycol, polyoxymethylene glycols, hemiformals, methylal and polyoxymethylene glycol dimethyl ethers (POMDME$_{n>1}$), and a high boiler fraction b2 comprising polyoxymethylene glycols, high-boiling hemiformals (HF$_{n>1}$) and high-boiling polyoxymethylene glycol dimethyl ethers (POMDME$_{n>4}$), and recycling the high boiler fraction b2 into the reactor (step a));

c) feeding the low boiler fraction b1 into a first distillation column and separating into a low boiler fraction c1 comprising formaldehyde, water, methylene glycol, methanol, hemiformals, methylal, di-, tri- and tetraoxymethylene glycol dimethyl ether (POMDME$_{n=2,3,4}$), and a high boiler fraction c2 comprising polyoxymethylene glycols, high-boiling hemiformals (HF$_{n>1}$) and high-boiling polyoxymethylene glycol dimethyl ethers (POMDME$_{n>4}$), and recycling the high boiler fraction c2 into the reactive evaporator (step b));

d) feeding the low boiler fraction c1 into a second distillation column and separating into a low boiler fraction d1 comprising formaldehyde, water, methanol, polyoxymethylene glycols, hemiformals, methylal and dioxymethylene glycol dimethyl ether (POMDME$_{n=2}$), and a high boiler fraction d2 substantially consisting of formaldehyde, water, methylene glycol, polyoxymethylene glycols, tri- and tetraoxymethylene glycol dimethyl ether (POMDME$_{n=3,4}$);

e) feeding the high boiler fraction d2 into a phase separation apparatus and separating into an aqueous phase e1 substantially consisting of formaldehyde, water, methylene glycol and polyoxymethylene glycols, and an organic phase e2 comprising tri- and tetraoxymethylene glycol dimethyl ether (POMDME$_{n=3,4}$);

f) feeding the organic phase e2 into a third distillation column and separating into a low boiler fraction f1 substantially consisting of formaldehyde, water, methylene glycol and polyoxymethylene glycols, and a high boiler fraction f2 substantially consisting of tri- and tetraoxymethylene glycol dimethyl ether (POMDME$_{n=3,4}$);

g) optionally feeding the aqueous phase e1 into a fourth distillation column and separating into a low boiler fraction g1 substantially consisting of formaldehyde, water, methylene glycol and polyoxymethylene glycols, and a high boiler fraction substantially consisting of water.

Owing to the large number of components and the large number of chemical equilibrium reactions proceeding simultaneously, the distillative separation of the mixture which leaves the reactor and comprises formaldehyde, water, methylene glycol, polyoxymethylene glycols, methanol, hemiformals, methylal and polyoxymethylene glycol dimethyl ethers is not apparent to the person skilled in the art and is a highly demanding problem. Merely from the boiling points of the components present, it is possible to make only a few statements with regard to their possible separation for formaldehydic mixtures. The reasons for this are chemical equilibrium reactions which proceed in the presence of water and methanol and lead to products including polyoxymethylene glycols and hemiformals. These reactions are subject firstly to limitation by the chemical equilibrium and secondly to kinetic control. Moreover, reactive azeotropes are formed which lead to complex phase equilibria.

In a step a), aqueous formaldehyde solution and methanol are fed into a reactor and converted to a mixture a comprising formaldehyde, water, methylene glycol, polyoxymethylene glycols, methanol, hemiformals, methylal and polyoxymethylene glycol dimethyl ethers.

In step a), commercial aqueous formaldehyde solution may be used directly or can be concentrated beforehand, for example as described in EP-A 1 063 221. In general, the formaldehyde concentration of the aqueous formaldehyde solution used in the process according to the invention is from 20 to 60% by weight. Methanol is preferably used in pure form. The presence of small amounts of other alcohols such as ethanol is not troublesome. It is possible to use methanol which comprises up to 30% by weight of ethanol.

Water, monomeric (free) formaldehyde, methylene glycol (MG) and oligomeric polyoxymethylene glycols of different chain length (MG$_{n>1}$) are present in aqueous solutions alongside one another in a thermodynamic equilibrium which is characterized by a particular distribution of the polyoxymethylene glycols of different length. The term "aqueous formaldehyde solution" also relates to formaldehyde solutions which comprise virtually no free water, but rather substantially only chemically bound water in the form of methylene glycol or in the terminal OH groups of the polyoxymethylene glycols. This is the case especially in concentrated formaldehyde solutions. Polyoxymethylene glycols may have, for example, from two to nine oxymethylene units. In aqueous formaldehyde solutions, dioxymethylene glycol, trioxymethylene glycol, tetraoxymethylene glycol, pentaoxymethylene glycol, hexaoxymethylene glycol, heptaoxymethylene glycol, octaoxymethylene glycol and nonaoxymethylene glycol may thus be present alongside one another. The distribution is concentration-dependent. For instance, the maximum of the distribution in dilute formaldehyde solutions is at homologs of low chain length, while it is at homologs of higher chain length in concentrated formaldehyde solutions. The equilibrium can be shifted toward longer-chain (higher molecular weight) polyoxymethylene glycols by water removal, for example by simple distillation in a film evaporator. The equilibrium is established at a finite rate by the intermolecular condensation of methylene glycol and low molecular weight polyoxymethylene glycols with elimination of water to give higher molecular weight polyoxymethylene glycols.

Formaldehyde reacts with methanol to give polyoxymethylene glycol dimethyl ethers by the overall reaction equation (1):

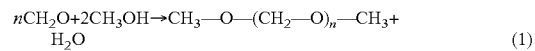

$$n\mathrm{CH_2O} + 2\mathrm{CH_3OH} \rightarrow \mathrm{CH_3-O-(CH_2-O)}_n-\mathrm{CH_3} + \mathrm{H_2O} \qquad (1)$$

The acidic catalyst used may be a homogeneous or heterogeneous acidic catalyst. Suitable acidic catalysts are mineral acids such as substantially anhydrous sulfuric acid, sulfonic acids such as trifluoromethanesulfonic acid and para-toluenesulfonic acid, heteropolyacids, acidic ion exchange resins, zeolites, aluminosilicates, silicon dioxide, aluminum oxide, titanium dioxide and zirconium dioxide. Oxidic catalysts may, in order to increase their acid strength, be doped with sulfate or phosphate groups, generally in amounts of from 0.05 to 10% by weight. The reaction may be carried out in a stirred tank reactor (CSTR) or a tubular reactor. When a heterogeneous catalyst is used, preference is given to a fixed bed reactor. When a fixed catalyst bed is used, the product mixture can subsequently be contacted with an anionic exchange resin in order to obtain a substantially acid-free product mixture. In the less advantageous case, a reactive distillation may also be used.

The reaction is effected generally at a temperature of from 0 to 200° C., preferably from 50 to 150° C., and a pressure of from 1 to 20 bar, preferably from 2 to 10 bar.

According to the overall reaction equation (2), polyoxymethylene glycols are formed. According to equation (3), polyoxymethylene glycol monomethyl ethers (hemiformals, $HF_n$) are formed.

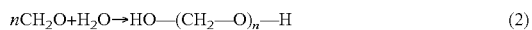

$$nCH_2O + H_2O \rightarrow HO-(CH_2-O)_n-H \qquad (2)$$

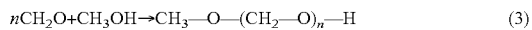

$$nCH_2O + CH_3OH \rightarrow CH_3-O-(CH_2-O)_n-H \qquad (3)$$

The condensation and chain-building reactions involved in the formation of the polyoxymethylene glycols, hemiformals and polyoxymethylene glycol dimethyl ethers are equilibrium reactions and therefore also proceed in reverse direction (depending on the position of the chemical equilibrium) as cleavage and chain-termination reactions. Thus, each of the distillation steps realized in the process according to the invention should be viewed as a complex reactive distillation.

In a step b), the reaction mixture a is fed into a reactive evaporator and separated into a low boiler fraction b1 comprising formaldehyde, water, methanol, methylene glycol, polyoxymethylene glycols, hemiformals, methylal and polyoxymethylene glycol dimethyl ethers ($POMDME_{n>1}$), and a high boiler fraction b2 comprising polyoxymethylene glycols, hemiformals ($HF_{n>1}$) and polyoxymethylene glycols ($POMDME_{n>3}$). The high boiler fraction b2 is returned to the reactor (step a).

The reactive evaporator constitutes the bottom evaporator of the first distillation column. The fraction c2 effluxing from the first distillation column comprises polyoxymethylene glycols, high-boiling hemiformals ($HF_{n>1}$) and high-boiling polyoxymethylene glycols ($POMDME_{n>4}$). This fraction mixes in the reactive evaporator with the reaction mixture a which comprises a higher proportion of water, methanol, polyoxymethylene glycols, hemiformals and polyoxymethylene glycol dimethyl ethers of shorter chain length. Thus, in the reactive evaporator, this leads to cleavage of long-chain components to components of shorter chain length. The reactive evaporator is generally operated at the pressure of the first column. However, it can also be operated at higher pressure. The operating pressure of the reactive evaporator is generally from 0.1 to 20 bar, preferably from 0.2 to 10 bar; the operating temperature is generally from 50 to 320° C., preferably from 80 to 250° C.

The distillation columns used in the steps c), d), f) and g) described below are columns of customary design. Useful columns are columns with random packing, tray columns and columns with structured packing; preference is given to tray columns and columns with structured packing. The term "low boiler fraction" is used for the mixture withdrawn in the upper section, the term "high boiler fraction" for that withdrawn in the lower section of the column. In general, the low boiler fraction is withdrawn at the top of the column, the high boiler fraction at the bottom of the column. However, this is not obligatory. It is also possible to withdraw the side draws in the stripping or rectifying section of the column.

In a step c), the low boiler fraction b1 is fed into a first distillation column and separated into a low boiler fraction c1 comprising formaldehyde, water, methylene glycol, methanol, hemiformals, methylal, di-, tri- and tetraoxymethylene glycol dimethyl ether ($POMDME_{n=2,3,4}$), and a high boiler fraction c2 comprising polyoxymethylene glycols, high-boiling hemiformals ($HF_{n>1}$) and high-boiling polyoxymethylene glycol dimethyl ethers ($POMDME_{n>4}$). The high boiler fraction c2 is returned to the reactive evaporator (step b).

The first distillation column generally has from 2 to 50 plates, preferably from 5 to 20 plates. It is operated at a pressure of from 0.1 to 10 bar, preferably from 0.2 to 6 bar. The top temperature is generally from 0 to 260° C., preferably from 20 to 230° C.; the bottom temperature is the temperature of the reactive evaporator.

In a step d), the low boiler fraction c1 is fed into a second distillation column and separated into a low boiler fraction d1 comprising formaldehyde, water, methanol, polyoxymethylene glycols, hemiformals, methylal and dioxymethylene glycol dimethyl ether ($POMDME_{n=2}$), and a high boiler fraction d2 substantially consisting of formaldehyde, water, methylene glycol, polyoxymethylene glycols, tri- and tetraoxymethylene glycol dimethyl ether ($POMDME_{n=3,4}$).

"Substantially consisting of" here and hereinbelow means that the fraction in question consists to an extent of at least 90% by weight, preferably to an extent of at least 95% by weight, of the components mentioned. The high boiler fraction d2 comprises in particular virtually no dioxymethylene glycol dimethyl ether. Its content in the high boiler fraction d2 is generally <3% by weight.

The second distillation column generally has from 1 to 50 plates, preferably from 1 to 20 plates. It is operated at a pressure of from 0.1 to 10 bar, preferably from 0.2 to 6 bar. The top temperature is generally from 0 to 160° C., preferably from 20 to 130° C.; the bottom temperature is generally from 50 to 260° C., preferably from 80 to 220° C.

In general, the low boiler fraction d1 is returned to the reactor (step a)).

In a step e), the high boiler fraction d2 is fed into a phase separation apparatus and separated into an aqueous phase e1 substantially consisting of formaldehyde, water, methylene glycol and polyoxymethylene glycols and an organic phase e2 comprising tri- and tetraoxymethylene glycol dimethyl ether ($POMDME_{n=3,4}$). The organic phase e2 additionally likewise comprises formaldehyde, water, methylene glycol and polyoxymethylene glycols.

In a step f), the organic phase e2 is fed into a third distillation column and separated into a low boiler fraction f1 substantially consisting of formaldehyde, water, methylene glycol and polyoxymethylene glycols, and a high boiler fraction f2 substantially consisting of tri- and tetraoxymethylene glycol dimethyl ether ($POMDME_{n=3,4}$).

The third distillation column generally has from 1 to 100 plates, preferably from 1 to 50 plates. It is operated at a pressure of from 0.1 to 10 bar, preferably from 0.2 to 6 bar. The top temperature is generally from 0 to +160° C., preferably from 20 to 130° C.; the bottom temperature is generally from +100 to +260° C., preferably from 150 to 240° C.

The high boiler fraction f2 constitutes the product of value of the process according to the invention. It may comprise more than 99% by weight of $POMDME_{n=3,4}$.

In general, in a further (optional) step g), the aqueous phase e1 is worked up further. To this end, it is fed into a fourth distillation column and separated into a low boiler fraction g1 substantially consisting of formaldehyde, water, methylene glycol and polyoxymethylene glycols, and a high boiler fraction substantially consisting of water.

The fourth distillation column generally has from 1 to 30 plates, preferably from 1 to 20 plates. It is operated at a pressure of from 0.1 to 10 bar, preferably from 0.2 to 6 bar. The top temperature is generally from −0 to +120° C., preferably from 20 to 100° C.; the bottom temperature is generally from +40 to +180° C., preferably from 60 to 150° C.

The low boiler fractions f1 and/or g1 may be returned as recycle streams to the second distillation column (step d)). They are preferably returned to the second distillation column. The low boiler fractions f1 and/or g1 may also be returned as recycle streams to the reactor (step a)).

The invention is illustrated by the drawing.

The FIGURE shows a preferred variant of the process according to the invention.

Aqueous formaldehyde solution 1 and methanol 2 are fed into the reactor 3 and converted to a mixture 4 comprising formaldehyde, water, methylene glycol, polyoxymethylene glycols, methanol, hemiformals, methylal and polyoxymethylene glycol dimethyl ethers. The reaction mixture 4 is separated in the reactive evaporator 5 into a low boiler fraction 7 comprising formaldehyde, water, methanol, methylene glycol, polyoxymethylene glycols, hemiformals, methylal and polyoxymethylene glycol dimethyl ethers, and a high boiler fraction 6 comprising polyoxymethylene glycols, high-boiling hemiformals and high-boiling polyoxymethylene glycols. The high boiler fraction 6 is recycled into the reactor 3. Low boiler fraction 7 separated in the first distillation column 8 into a low boiler fraction 10 comprising formaldehyde, water, methylene glycol, methanol, hemiformals, methylal, di-, tri- and tetraoxymethylene glycol dimethyl ether, and a high boiler fraction 9 comprising polyoxymethylene glycols, high-boiling hemiformals ($HF_{n>1}$) and high-boiling polyoxymethylene glycols. The high boiler fraction 9 is returned to the reactive evaporator 5. The low boiler fraction 10 is separated in the second distillation column into a low boiler fraction 12 comprising formaldehyde, water, methanol, polyoxymethylene glycols, hemiformals, methylal and dioxymethylene glycol dimethyl ether, and a high boiler fraction 13 composed of formaldehyde, water, methylene glycol, polyoxymethylene glycols, tri- and tetraoxymethylene glycol dimethyl ether. The low boiler fraction 12 is returned to the reactor 3. The high boiler fraction 13 is separated in the phase separation apparatus 22 into an aqueous phase 18 composed of formaldehyde, water, methylene glycol and polyoxymethylene glycols, and an organic phase 14 comprising tri- and tetraoxymethylene glycol dimethyl ether and additionally formaldehyde, water, methylene glycol and polyoxymethylene glycols. The organic phase 14 is separated in the fourth distillation column 15 into a low boiler fraction 16 composed of formaldehyde, water, methylene glycol and polyoxymethylene glycols, and a high boiler fraction 17 consisting of tri- and tetraoxymethylene glycol dimethyl ether. The high boiler fraction 17 is obtained as the product of value. The low boiler fraction 16 is returned to the second distillation column 11. The aqueous phase 18 is separated in the fifth distillation column 19 into a low boiler fraction 20 composed of formaldehyde, water, methylene glycol and polyoxymethylene glycols, and a high boiler fraction 21 composed of water. The low boiler fraction 20 is returned to the second distillation column 11.

What is claimed is:

1. A process for preparing tri- and tetraoxymethylene glycol dimethyl ether ($POMDME_{n=3,4}$) by reacting formaldehyde with methanol and subsequently working up the reaction mixture by distillation, comprising the steps of:

a) feeding aqueous formaldehyde solution and methanol into a reactor and reacting to give a mixture a comprising formaldehyde, water, methylene glycol (MG), polyoxymethylene glycols ($MG_{n>1}$), methanol, hemiformals (HF), methylal ($POMDME_{n=1}$) and polyoxymethylene glycol dimethyl ethers ($POMDME_{n>1}$);

b) feeding the reaction mixture a into a reactive evaporator and separating into a low boiler fraction b1 comprising formaldehyde, water, methanol, methylene glycol, polyoxymethylene glycols, hemiformals, methylal and polyoxymethylene glycol dimethyl ethers ($POMDME_{n>1}$), and a high boiler fraction b2 comprising polyoxymethylene glycols, hemiformals ($HF_{n>1}$) and polyoxymethylene glycol dimethyl ethers ($POMDMF_{n>3}$), and recycling the high boiler fraction b2 into the reactor (step a));

c) feeding the low boiler fraction b1 into a first distillation column and separating into a low boiler fraction c1 comprising formaldehyde, water, methylene glycol, methanol, hemiformals, methylal, di-, tri- and tetraoxymethylene glycol dimethyl ether ($POMDME_{n=2,3,4}$), and a high boiler fraction c2 comprising polyoxymethylene glycols, high-boiling hemiformals ($HF_{n>1}$) and high-boiling polyoxymethylene glycol dimethyl ethers ($POMDME_{n>4}$), and recycling the high boiler fraction c2 into the reactive evaporator (step b));

d) feeding the low boiler fraction c1 into a second distillation column and separating into a low boiler fraction d1 comprising formaldehyde, water, methanol, polyoxymethylene glycols, hemiformals, methylal and dioxymethylene glycol dimethyl ether ($POMDME_{n=2}$), and a high boiler fraction d2 substantially consisting of formaldehyde, water, methylene glycol, polyoxymethylene glycols, tri- and tetraoxymethylene glycol dimethyl ether ($POMDME_{n=3,4}$);

e) feeding the high boiler fraction d2 into a phase separation apparatus and separating into an aqueous phase e1 substantially consisting of formaldehyde, water, methylene glycol and polyoxymethylene glycols, and an organic phase e2 comprising tri- and tetraoxymethylene glycol dimethyl ether ($POMDME_{n=3,4}$);

f) feeding the organic phase e2 into a third distillation column and separating into a low boiler fraction f1 substantially consisting of formaldehyde, water, methylene glycol and polyoxymethylene glycols, and a high boiler fraction f2 substantially consisting of tri- and tetraoxymethylene glycol dimethyl ether ($POMDME_{n=3,4}$);

g) optionally feeding the aqueous phase e1 into a fourth distillation column and separating into a low boiler fraction g1 substantially consisting of formaldehyde, water, methylene glycol and polyoxymethylene glycols, and a high boiler fraction substantially consisting of water.

2. The process according to claim 1, wherein the low boiler fraction d1 is returned as a recycle stream to step a) of the process.

3. The process according to claim 1, wherein the low boiler fractions f1 and/or g1 are returned as recycle streams to the second distillation column in step d) of the process.

4. The process according to claim 1, wherein the low boiler fractions f1 and/or g1 are returned as recycle streams to step a) of the process.

* * * * *